United States Patent [19]

Geisler

[11] 4,411,841
[45] Oct. 25, 1983

[54] PREPARATION OF NOVEL PERFLUORINATED SULPHONIC ACID FLUORIDES

[75] Inventor: Klaus Geisler, Bonn, Fed. Rep. of Germany

[73] Assignee: Bayer Aktiengesellschaft, Leverkusen, Fed. Rep. of Germany

[21] Appl. No.: 315,766

[22] Filed: Oct. 28, 1981

[30] Foreign Application Priority Data

Nov. 18, 1980 [DE] Fed. Rep. of Germany ....... 3043427

[51] Int. Cl.$^3$ .......................................... C07C 143/70
[52] U.S. Cl. .............................. 260/543 F; 260/543 R
[58] Field of Search ........................ 260/543 F, 543 R

[56] References Cited

U.S. PATENT DOCUMENTS

| | | | |
|---|---|---|---|
| 2,219,006 | 10/1940 | Delfs et al. ........................... | 260/329 |
| 3,623,963 | 11/1971 | Voss et al. ............................. | 204/59 |
| 3,723,512 | 3/1973 | Niederprum et al. .......... | 260/501.15 |
| 3,821,290 | 6/1974 | Auello et al. .................... | 260/543 F |

FOREIGN PATENT DOCUMENTS 1099240 1/1968 United Kingdom .

OTHER PUBLICATIONS

Temple, S., Journal of Organic Chemistry, vol. 33, No. 1, 1968, pp. 344–346.

*Primary Examiner*—Donald B. Moyer
*Assistant Examiner*—Frederick W. Pepper
*Attorney, Agent, or Firm*—Sprung, Horn, Kramer & Woods

[57] ABSTRACT

Electrochemical fluorination of a thiophene-1,1-dioxide derivative of the formula

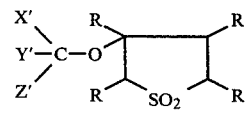

produces the novel perfluorinated sulphonic acid fluoride of the formula

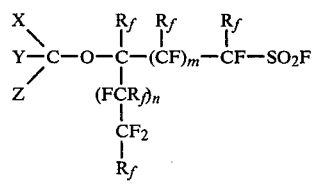

in which X, Y and Z each independently is F, a perfluoroalkyl group having 1 to 8 C-atoms in which one or more $CF_2$ groups may optionally be replaced by oxygen, the oxygen atoms being separated by at least one $CF_2$ group, optionally perfluoroalkyl-substituted cycloperfluoroalkyl group having 5 to 12 C-atoms in which one or more $CF_2$ groups may be replaced by oxygen, or X and Y together denote an optionally perfluoroalkyl-substituted cycloperfluoroalkyl group in which one or more $CF_2$ groups may be replaced by oxygen, $R_f$ each independently is F or a perfluoroalkyl group having 1 to 3 C-atoms, and n and m each independently is 0 or 1.

The products are useful as surface active agents.

12 Claims, No Drawings

PREPARATION OF NOVEL PERFLUORINATED SULPHONIC ACID FLUORIDES

This invention relates to perfluorinated sulphonic acid fluorides corresponding to the general formula (I):

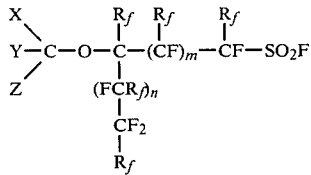

wherein X, Y and Z independently denote F, a perfluoroalkyl group having 1–8 C-atoms in which one or more $CF_2$ groups may be replaced by oxygen, the oxygen atoms being separated by at least one $CF_2$ group; or an optionally perfluoroalkyl-substituted cycloperfluoroalkyl group having 5–12 C-atoms in which one or more $CF_2$ groups may be replaced by oxygen; or X and Y together denote an optionally perfluoroalkyl-substituted cycloperfluoroalkyl group in which one or more $CF_2$ groups may be replaced by oxygen; $R_f$ independently denotes F or a perfluoroalkyl group having 1–3 C-atoms; and n and m denote the number 0 or 1. The invention also relates to a process for the preparation of the aforesaid perfluorinated sulphonic acid fluorides.

In the conventional electrofluorination of alkyl sulphonic acid halides to perfluoroalkylsulphonic acid fluorides, the yields diminish with increasing chain length owing to cleavages or rearrangements of the carbon structure and polymerization accompanied by the formation of sludge. Only unsatisfactory yields are obtained from the process, particularly in the case of the technically interesting relatively long chain perfluoroalkylsulphonyl fluorides (see e.g. J. Chem. Soc., 1957, 2640). Added to this is the fact that the starting compounds, alkyl-1-sulphonic acid fluorides or -chlorides, are only obtainable by elaborate, multistage processes in which numerous unusable by-products are formed. Thus, for example, the synthesis of $C_8H_{17}SO_2F$ is accompanied by the formation of at least 1.7 times the quantity of NaCl, which must either be carried away with the effluent or removed by costly purification methods.

It is therefore an object of the present invention to synthesize new perfluorinated sulphonic acid fluorides having at least one oxygen atom in an ether function by an improved process in which the desired compounds are obtained in high yields compared with those of the known processes and from easily available starting compounds.

The solution to this problem was surprisingly found to lie in the electrochemical fluorination of the addition products, readily available according to German Pat. No. 682 079, of primary, secondary and tertiary alcohols with Δ3-dihydrothiophene-1,1-dioxides (e.g. sulpholene) corresponding to the general formula (II):

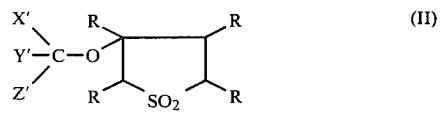

wherein X', Y' and Z' independently denote H, an alkyl group with 1–8 C-atoms in which one or more $CH_2$ groups may be substituted by oxygen, the oxygen atoms being separated by at least one $CH_2$ group; an optionally alkyl-substituted cycloalkyl group having 5–12 C-atoms in which one or more of the $CH_2$ groups may be replaced by oxygen; or X' and Y' together denote an optionally alkyl-substituted cycloalkyl group in which one or more $CH_2$ groups may be replaced by oxygen; and each R independently denotes H or an alkyl group having 1 to 3 C-atoms.

Electrochemical fluorination of cyclic sulphones to perfluoroalkyl sulphonyl fluorides has been disclosed in British Pat. No. 1,099,240 and Belgian Pat. No. 747,306, but it was totally unexpected to find that these substituted sulphones could also be electrofluorinated to perfluoroalkyl-substituted open-chained sulphonyl fluorides without splitting of the ether bond since one of the sulphur-carbon bonds is split by fluorination.

Preferred starting compounds corresponding to the general formula (II) are those in which Z' denotes H, X' and Y' denote H or a short-chained alkyl group having 1 to 6 C-atoms in which one or at the most two $CH_2$ groups may be replaced by oxygen, or X' and Y' together denote an optionally $C_{1-4}$-alkyl-substituted cycloalkyl group having 5 to 8 carbon atoms and individual $CH_2$ groups may be replaced by oxygen, and R independently denotes H or a methyl group. These give rise to the preferred perfluoroalkyl sulphonic acid fluorides of formula (I) wherein X and Y each independently is F, perfluoroalkyl with 1 to 6 C-atoms in which one $CF_2$ group or two separated $CF_2$ groups may be replaced by oxygen, or X and Y together are an optionally perfluoro-$C_{1-4}$-alkyl-substituted cycloalkyl group with 5 to 8 carbon atoms of which individual $CF_2$ groups may be replaced by oxygen, and Z is F, and $R_f$ each independently is F or fluoromethyl.

The following are examples of starting compounds used in the process according to the invention: 3-methoxy-tetrahydrothiophene-1,1-dioxide, 3-ethoxy-tetrahydrothiophene-1,1-dioxide, 3-propoxy-tetrahydrothiophene-1,1-dioxide, 3-i-propoxy-tetrahydrothiophene-1,1-dioxide, 3-n-butoxy-tetrahydrothiophene-1,1-dioxide, 3-sec-butoxy-tetrahydrothiophene-1,1-dioxide, 3-tert.-butoxy-tetrahydrothiophene-1,1-dioxide, 3-(2-ethyl)-hexoxytetrahydrothiophene-1,1-dioxide, 3-(2-methoxy)-ethoxy-tetrahydrothiophene 1,1-dioxide, 3-(2-ethoxy)-ethoxy-tetrahydrothiophene-1,1-dioxide, 3-cyclohexoxy-tetrahydrothiophene-1,1-dioxide, 3-(4-methyl)-cyclohexoxy-tetrahydrothiphene-1,1-dioxide, 3-(4-methoxy)-cyclohexoxy-tetrahydrothiophene-1,1-dioxide, 3-methyl-4-methoxy-tetrahydrothiophene-1,1-dioxide, 2-ethyl-3-methoxy-tetrahydrothiophene-1,1-dioxide, 3-methyl-3-methoxy-tetrahydrothiophene-1,1-dioxide and 2-methyl-3-methoxy-tetrahydrothiophene-1,1-dioxide.

The process of electrochemical fluorination has been described in some detail, inter alia in U.S. Pat. Nos. 2,717,871 and 2,519,983, in Houben-Weyl, Methoden der organischen Chemie, Vol. C, part 3, pages 42–50, and in German Offenlegungsschriften Nos. 2,442,106 and 2,725,211. The process according to the invention is carried out with a substrate concentration of about 0.2 to 10% by weight in hydrogen fluoride, an electrolytic voltage of about 4.5 to 15 V, a current density of about 4 to 20 mA/cm$^2$ of active anode surface and a temperature of about $-20°$ C. to $50°$ C., preferably about $0°$ to $15°$ C.

The starting compounds corresponding to the general formula (II) are dissolved in hydrogen fluoride at a concentration of 0.2 to 10% by weight at the beginning of electrolysis. The solution obtained conduct the electric current. Hydrogen fluoride and organic substrate are replaced either intermittently of continuously during electrolysis at the rate at which they are used up. Ascending reflux condensers charged with cooling brine are provided to free the cathodically formed hydrogen from most of the hydrogen fluoride carried with it, which is returned to the electrolytic cell. The crude perfluoro products accumulate at a low level of the electrolytic apparatus as specifically heavy liquids and are removed from time to time.

By means of the invention, perfluorinated sulphonic acid fluorides corresponding to the general formula (I):

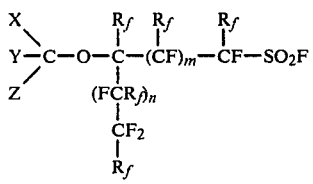

wherein X, Y, Z, $R_f$ and n and m have the meaning indicated above are obtained in high yields compared with those achieved in the preparation of perfluoroalkylsulphonyl fluorides of the same chain length. The following are examples of compounds prepared according to the invention: 4-oxa-3-trifluoromethyl-perfluoropentyl-1-sulphofluoride, 3-oxa-2-pentafluoroethyl-perfluorobutyl-1-sulphofluoride, 4-oxa-3-trifluoromethylperfluorohexyl-1-sulphofluoride, 3-oxa-2-pentafluoroethyl-perfluoropentyl-1-sulphofluoride, 4-oxa-3,5-bistrifluoromethyl-perfluorohexyl-1-sulphofluoride, 3-oxa-2-pentafluoroethyl-4-trifluoromethylperfluoropentyl-1-sulphofluoride, 4-oxa-3-trifluoromethyl-6-pentafluoroethyl-perfluorodecyl-1-sulphofluoride, 3-oxa-2,5-bis-pentafluoroethyl-perfluorononyl-1-sulphofluoride, 4,7-dioxa-3-trifluoromethyl-perfluorooctyl-1-sulphofluoride, 3,6-dioxa-2-pentafluoroethyl-perfluoroheptyl-1-sulphofluoride, 4-oxa-3-trifluoromethyl-4-perfluorocyclohexyl-perfluorobutyl-1-sulphofluoride, 3-oxa-2-pentafluoroethyl-3-perfluorocyclohexyl-perfluoropropyl-1-sulphofluoride, 4-oxa-3-pentafluoroethyl-perfluoropentyl-1-sulphofluoride and 3-oxa-1-trifluoromethyl-2-pentafluoroethyl-perfluorobutyl-1-sulphofluoride.

According to $^{19}$F-NMR and gas chromatographic investigations, the isomeric compounds (I) wherein m=1, n=0 and wherein m=0, n=1, respectively, are obtained from one and the same starting compound (II) in a proportion by weight of about 1:4.

The perfluorinated sulphonic acid fluorides corresponding to the general formula (I) are useful for numerous purposes. According to German Offenlegungsschrift No. 1,929,665 (equivalent to U.S. Pat. No. 3,723,512), for example, they may be converted into the tetraethyl ammonium salt of the given oxaperfluorosulphonic acid.

The tetraethyl ammonium salt can be produced according to Examples 1 or 2 of U.S. Pat. No. 3,723,512. In Example 1 of U.S. Pat. No. 3,723,572 tetraethylammonium-perfluorobutylsulfonate was produced as follows:

18.2 g (0.06 mol) of perfluorobutylsulfonyl fluoride were dissolved in 50 ml of ether, and 6.6 g (0.061 mol) of triethylamine and 4 g (0.0228 mol) of methyltriethoxysilane were added. The solution which is at first clear become cloudy after 2 hours and a slight increase in temperature occurred. After 24 hours, the precipitated salt was filtered off, washed with ether and dried in a vacuum of 0.4 mm Hg. 18.5 g (approximately 70.5 percent yield) of a white salt of the formula $[(C_2H_5)_4N]^+[C_4F_9SO_3]^-$, which was confirmed by the $^1$H and $^{19}$F nuclear magnetic resonance spectrum, were obtained.

In Example 2 of U.S. Pat. No. 3,723,512 tetraethylammonium-perfluorobutylsulfonate was produced as follows:

90.6 g (0.3 mol) of perfluorobutylsulfonyl fluoride, 30.6 g (0.303 mol) of triethylamine and 22.2 g (0.15 mol) of dimethyldiethoxysilane were successively dissolved in 350 ml of diethylether. The temperature of the reaction mixture rose to $27°$ C. Crystallization of the quaternary ammonium salt started after a few hours and was complete within 2 days. The crystals were filtered off, washed with diethylether and finally freed from the adhering solvent in a vacuum of 1 mm Hg. Yield 111.8 g (78.5 percent of theoretical), m.p. $180°-183°$ C. The product was identified as $[N(C_2H_5)_4]^+[C_4F_9SO_3]$ by its IR, $^1$H-NMR and $^{19}$F-NMR spectrum.

Analyses: Calculated: 33.6% C; 4.7% H; 3.3% N; 7.5% S; 39.8% F. Found: 33.0% C; 4.3% H; 3.4% N; 7.5% S; 37.1% F.

Used at only very low concentrations, they impart a low surface tension to water and may therefore be used as wetting agents and levelling agents. Alkaline or ammoniacal hydrolysis results in the analogous alkali metal and ammonium salts, which are also used as surface active agents. The reaction with anhydrous ammonia and primary amines results in oxaperfluoroalkylsulphonamides, which may be used as starting compounds for imparting a dirt repellent, water repellent and oil repellent finish to leather, paper and textile surfaces.

The following examples illustrate the invention without, however, limiting it.

EXAMPLE 1

Electrochemical fluorination of 3-n-butoxy-tetrahydrothiophene-1,1-dioxide

The addition product of $\Delta^3$-dihydrothiophene-1,1-dioxide and n-butanol is prepared according to German Pat. No. 682,079 (equivalent to U.S. Pat. No. 2,219,006). The resulting 3-n-butoxy-tetrahydrothiophene-1,1-dioxide boils at $123°-130°$ C. and 10 mbar.

In Example 2 of U.S. Pat. No. 2,219,006, methanol was utilized, but the methyl alcohol is replaceable with any other alcohol. In such Example 2, 80 parts of potassium hydroxide are dissolved in 2,000 parts of methanol. During 10 hours at $25°$ C. 4,000 parts of 3,4-dehydrocyclotetramethylene sulphone are added while stirring. Stirring is continued for a further 24 hours. Now first sulphuric acid is added until the liquid turns Congo paper blue and then potassium or magnesium carbonate is added in excess. The separated salts are removed by filtration and the ether which has probably the following constitution:

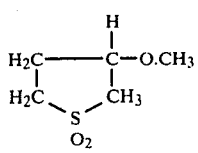

is obtained by distilling off the excess methanol. Distillation of the ether in vacuo yields a colorless, odorless liquid, boiling point 164° C. under a pressure of 12.5 mm. The ether is miscible with water and most organic solvents.

This compound is dissolved in hydrogen fluoride at an initial concentration of 2% by weight in an apparatus described in German Offenlegungsschrift No. 2,715,211 and electrolyzed at an average current density of 6 mA/cm$^2$ of anode surface for 35 days. Fresh hydrogen fluoride is added to replace the quantity used up, while 3-n-butoxytetrahydrothiophene-1,1-dioxide is replaced according to the current consumption. The crude perfluorinated product is discharged from the electrolyte system from time to time. A total of 27.9 kg of starting compound is put into the process and a total 40.6 kg of crude perfluorinated product is obtained.

Fractionating the crude perfluorinated product yields 23.3 kg of a 1:4 mixture of 4-oxa-3-trifluoromethyl-perfluoro-octyl-1-sulphofluoride and 3-oxa-2-pentafluoroethyl-perfluoroheptyl-1-sulphofluoride.

The yield, based on the quantity of 3-n-butoxytetrahydrothiphene-1,1-dioxide put into the process, is 31%.

EXAMPLE 2

Electrochemical fluorination of 3-isopropoxy-tetrahydrothiophene-1,1-dioxide

3-Isopropoxy-tetrahydrothiophene-1,1-dioxide is synthesized according to German Pat. No. 682,079 and electrolyzed as in Example 1. Using 30 kg of starting compounds, 28.4 kg of a 1:4 mixture of 4-oxa-3,5-bis-trifluoromethyl-perfluorohexyl-1-sulphofluoride and 3-oxa-2-pentafluoroethyl-4-trifluoromethyl-perfluoropentyl-1-sulphofluoride is obtained. This corresponds to a yield of 36%, based on the quantity of starting product.

EXAMPLE 3

Electrochemical fluorination of 3-methoxy-tetrahydrothiophene-1,1-dioxide

3-Methoxy-tetrahydrothiphene-1,1-dioxide is prepared as described in German Pat. No. 682,079. The compound is electrochemically fluorinated as in Example 1. 11 kg of starting product yield 11.6 kg of a 1:4 mixture of 4-oxa-3-trifluoromethyl-perfluoropentyl-1-sulphofluoride and 3-oxa-2-pentafluoroethyl-perfluorobutyl-1-sulphofluoride. This corresponds to a yield of 44%.

EXAMPLE 4

Electrochemical fluorination of 3-(2-methoxy)-ethoxytetrahydrothiophene-1,1-dioxide The starting compound is prepared according to German Pat. No. 682,079 and electrofluorinated as in Example 1. 16 kg of starting material yield 11.2 kg of a 1:4 mixture of 4,7-dioxa-3-trifluoromethyl-perfluorooctyl-1-sulphofluoride and 3,6-dioxa-2-pentafluoroethyl-perfluoroheptyl-1-sulphofluoride. This corresponds to a 28% yield.

EXAMPLE 5

Electrochemical fluorination of 3-cyclohexoxy-tetrahydrothiophene-1,1-dioxide

3-Cyclohexoxy-tetrahydrothiophene-1,1-dioxide is prepared in accordance with German Pat. No. 682,079 and electrochemically fluorinated as in Example 1. 14 kg of the starting material yield 8.2 kg of a 1:4 mixture of 4-oxa-3-trifluoromethyl-4-perfluorocyclohexyl-perfluorobutyl-1-sulphofluoride and 3-oxa-2-pentafluoroethyl-3-perfluorocyclohexyl-perfluoropropyl-1-sulphofluoride. The yield, based on the quantity of starting material put into the process, is 22%.

EXAMPLE 6

According to German Offenlegungsschrift No. 1,929.665 518 g (1 Mol) of a 1:4 mixture of 4-oxa-3-trifluoromethyl-perfluorooctyl-1-sulfofluoride and 3-oxa-2-pentafluoroethyl-perfluoroheptyl-1-sulfofluoride is reacted in 1 l of chlorobenzene with equimolar amounts of triethylamine 101 g and methyl-triethoxysilane (178 g). The white precipitate is filtered off and dried. 0.1 g of the isolated tetraethylammonium-salt of the corresponding above mentioned oxa-perfluoroalkylsulfonic acids imperts water an interfacial tension of 20.5 mN/m and may therefore be used as a tenside or a wetting agent.

It will be appreciated that the instant specification and examples are set forth by way of illustration and not limitation, and that various modification and changes may be made without departing from the spirit and scope of the present invention.

I claim:

1. A compound selected from the group consisting of 4-oxa-3-trifluoromethyl-perfluoropentyl-1-sulphofluoride, 3-oxa-2-pentafluoroethyl-perfluorobutyl-1-sulphofluoride, 4-oxa-3-trifluoromethyl-perfluorohexyl-1-sulphofluoride, 3-oxa-2-pentafluoroethyl-perfluoropentyl-1-sulphofluoride, 4-oxa-3,5-bis-trifluoromethyl-perfluorohexyl-1-sulphofluoride, 3-oxa-2-pentafluoroethyl-4-trifluoromethylperfluoropentyl-1-sulphofluoride, 4-oxa-3-trifluoromethyl-6-pentafluoroethyl-perfluorodecyl-1-sulphofluoride, 3-oxa-2,5-bis-pentafluoroethyl-perfluorononyl-1-sulphofluoride, 4,7-dioxa-3-trifluoromethyl-perfluorooctyl-1-sulphofluoride, 3,6-dioxa-2-pentafluoroethyl-perfluoroheptyl-1-sulphofluoride, 4-oxa-3-trifluoromethyl-4-perfluorocyclohexyl-perfluorobutyl-1-sulphofluoride, 3-oxa-2-pentafluoroethyl-3-perfluorocyclohexyl-perfluoropropyl-1-sulphofluoride, 4-oxa-3-pentafluoroethyl-perfluoropentyl-1-sulphofluoride and 3-oxa-1-trifluoromethyl-2-pentafluoroethyl-perfluorobutyl-1-sulphofluoride.

2. A compound according to claim 1, selected from the group consisting of
4-oxa-3-trifluoromethyl-perfluorooctyl-1-sulphofluoride,
3-oxa-2-pentafluoroethyl-perfluoroheptyl-1-sulphofluoride,
4-oxa-3,5-bis-trifluoromethyl-perfluorohexyl-1-sulphofluoride,
3-oxa-2-pentafluoroethyl-4-trifluoromethyl-perfluoropentyl-1-sulphofluoride, 4-oxa-3-trifluoromethyl-perfluoropentyl-1-sulphofluoride, 3-oxa-2-pentafluoroethyl-perfluorobutyl-1-sulphofluoride, 4,7-dioxa-3-trifluoromethyl-perfluorooctyl-1-sulphofluoride, 3,6-dioxa-2-pentafluoroethyl-perfluoroheptyl-1-sulphofluoride, 4-oxa-3-trifluoromethyl-4-perfluorocyclohexyl-perfluorobutyl-1-sulphofluoride and 3-oxa-2-pentafluoroethyl-3-perfluorocyclohexyl-1-sulphofluoride.

3. A compound according to claim 1, wherein such compound is 4-oxa-3-trifluoromethyl-perfluorooctyl-1-sulphofluoride.

4. A compound according to claim 1, wherein such compound is 3-oxa-2-pentafluoroethyl-perfluoroheptyl-1-sulphofluoride.

5. A compound according to claim 1, wherein such compound is 4-oxa-3,5-bis-trifluoromethyl-perfluorohexyl-1-sulphofluoride.

6. A compound according to claim 1, wherein such compound is 3-oxa-2-pentafluoroethyl-4-trifluoromethyl-perfluoropentyl-1-sulphofluoride.

7. A compound according to claim 1, wherein such compound is 4-oxa-3-trifluoromethyl-perfluoropentyl-1-sulphofluoride.

8. A compound according to claim 1, wherein such compound is 3-oxa-2-pentafluoroethyl-perfluorobutyl-1-sulphofluoride.

9. A compound according to claim 1, wherein such compound is 4,7-dioxa-3-trifluoromethyl-perfluorooctyl-1-sulphofluoride.

10. A compound according to claim 1, wherein such compound is 3,6-dioxa-2-pentafluoroethyl-perfluoroheptyl-1-sulphofluoride.

11. A compound according to claim 1, wherein such compound is 4-oxa-3-trifluoromethyl-4-perfluorocyclohexyl-perfluorobutyl-1-sulphofluoride.

12. A compound according to claim 1, wherein such compound is 3-oxa-2-pentafluoroethyl-3-perfluorocyclohexyl-perfluoropropyl-1-sulphofluoride.

* * * * *